(12) United States Patent
Zocca et al.

(10) Patent No.: US 9,603,515 B2
(45) Date of Patent: Mar. 28, 2017

(54) CATHETER FOR TRACHEO-BRONCHIAL SUCTION WITH VISUALIZATION MEANS

(76) Inventors: Mario Zocca, Verona (IT); Peter Young, Roydon Kinds Lynn Norfolk (GB)

( * ) Notice: Subject to any disclaimer, the term of this patent is extended or adjusted under 35 U.S.C. 154(b) by 162 days.

(21) Appl. No.: 13/148,561

(22) PCT Filed: Feb. 9, 2010

(86) PCT No.: PCT/IB2010/050590
§ 371 (c)(1),
(2), (4) Date: Aug. 18, 2011

(87) PCT Pub. No.: WO2010/089726
PCT Pub. Date: Aug. 12, 2010

(65) Prior Publication Data
US 2011/0313347 A1    Dec. 22, 2011

(30) Foreign Application Priority Data
Feb. 9, 2009   (GB) .................................. 0901945.6

(51) Int. Cl.
| | |
|---|---|
| *A61B 1/00* | (2006.01) |
| *A61B 1/04* | (2006.01) |
| *A61B 1/06* | (2006.01) |
| *A61B 1/267* | (2006.01) |
| *A61M 16/00* | (2006.01) |

(52) U.S. Cl.
CPC ........ *A61B 1/2676* (2013.01); *A61B 1/00052* (2013.01); *A61B 1/06* (2013.01)

(58) Field of Classification Search
USPC ........ 600/104, 106, 107, 114–116, 120–125, 600/136, 137, 139–142; 604/525; 128/200.26, 207.14
See application file for complete search history.

(56) References Cited

U.S. PATENT DOCUMENTS

| | | | |
|---|---|---|---|
| 4,351,328 A | | 9/1982 | Bodai |
| 4,384,570 A | * | 5/1983 | Roberts .......................... 600/187 |
| 4,569,344 A | | 2/1986 | Palmer |
| 4,697,894 A | * | 10/1987 | Takamura et al. ............ 359/503 |
| 4,708,126 A | * | 11/1987 | Toda et al. ..................... 600/132 |
| 5,083,549 A | * | 1/1992 | Cho et al. ...................... 600/108 |
| 5,285,778 A | | 2/1994 | Mackin |
| 5,733,242 A | * | 3/1998 | Rayburn et al. .............. 600/120 |

(Continued)

FOREIGN PATENT DOCUMENTS

EP       742026 A1 * 11/1996 ............... A61B 1/00

*Primary Examiner* — Ryan Henderson
(74) *Attorney, Agent, or Firm* — Tutunjian & Bitetto, P.C.

(57) ABSTRACT

A catheter for tracheal or bronchial suction including a unit for displaying the artificial airways, the trachea and the bronchial tree so as to allow the removal of secretions; in particular, the catheter for tracheal or bronchial suction includes optical fibers, a microcamera or another visualization technology positioned in the distal end. The operator can identify the position of the distal end, of the artificial airways, of the trachea and of the bronchial tree on the screen. Therefore, it is possible to ensure that the tube of the catheter is adjacent to or inside collections of fluid secretions or other material to be sucked up. The suction can be selectively applied to avoid damage to the mucosa and to facilitate the more complete elimination of secretions.

18 Claims, 6 Drawing Sheets

(56) References Cited

U.S. PATENT DOCUMENTS

| | | | |
|---|---|---|---|
| 5,846,183 A * | 12/1998 | Chilcoat | 600/136 |
| 5,863,286 A * | 1/1999 | Yabe et al. | 600/121 |
| 5,928,137 A | 7/1999 | Green | |
| 6,319,195 B1 * | 11/2001 | Nakaichi et al. | 600/120 |
| 6,929,600 B2 * | 8/2005 | Hill | 600/120 |
| 7,946,981 B1 * | 5/2011 | Cubb | 600/194 |
| 2002/0022769 A1 * | 2/2002 | Smith et al. | 600/188 |
| 2002/0077527 A1 * | 6/2002 | Aydelotte | A61B 1/00082 600/120 |
| 2002/0103419 A1 * | 8/2002 | Christopher | 600/156 |
| 2003/0078476 A1 * | 4/2003 | Hill | 600/160 |
| 2003/0168059 A1 * | 9/2003 | Pacey | 128/200.26 |
| 2004/0074491 A1 | 4/2004 | Hendricksen et al. | |
| 2004/0133073 A1 * | 7/2004 | Berci et al. | 600/112 |
| 2004/0220451 A1 | 11/2004 | Gravenstein et al. | |
| 2005/0090712 A1 * | 4/2005 | Cubb | 600/120 |
| 2005/0119527 A1 | 6/2005 | Banik et al. | |
| 2005/0177024 A1 | 8/2005 | Mackin | |
| 2005/0234437 A1 | 10/2005 | Baxter et al. | |
| 2005/0288665 A1 | 12/2005 | Woloszko | |
| 2006/0122460 A1 * | 6/2006 | Kamali | 600/120 |
| 2007/0038024 A1 * | 2/2007 | Nakamura et al. | 600/110 |
| 2007/0049794 A1 | 3/2007 | Glassenberg et al. | |
| 2007/0215162 A1 | 9/2007 | Glassenberg et al. | |
| 2008/0051628 A1 | 2/2008 | Pecherer et al. | |

\* cited by examiner

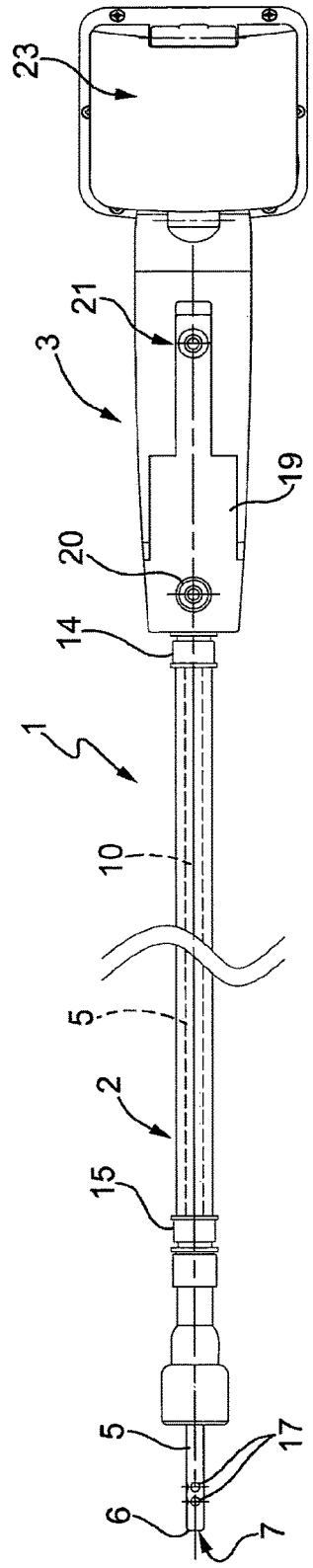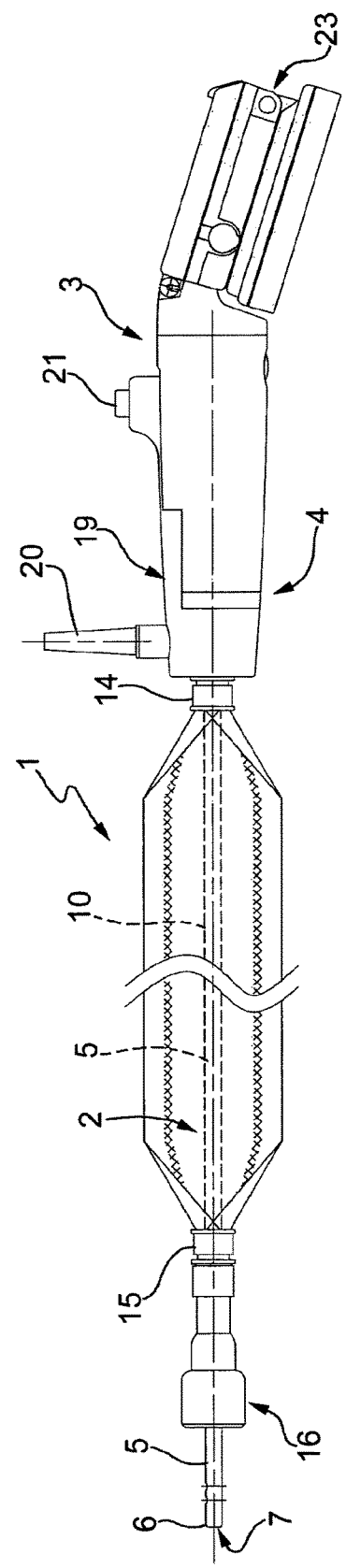

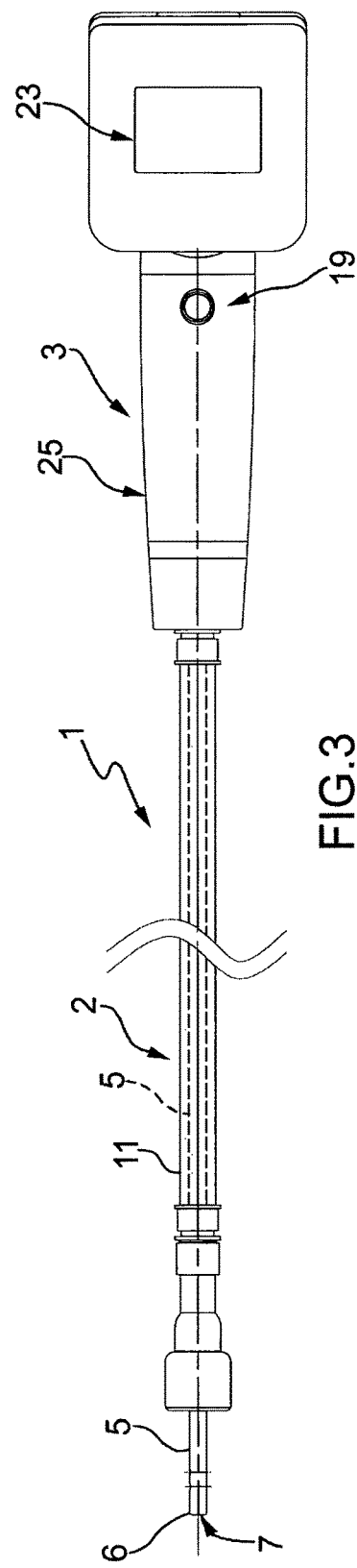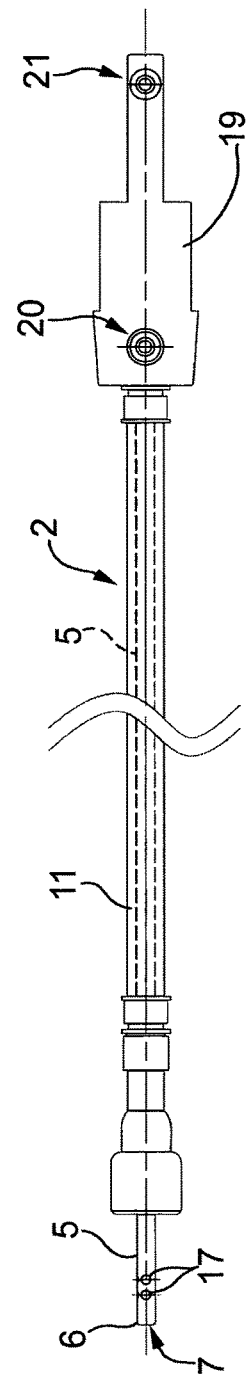
FIG.3
FIG.4

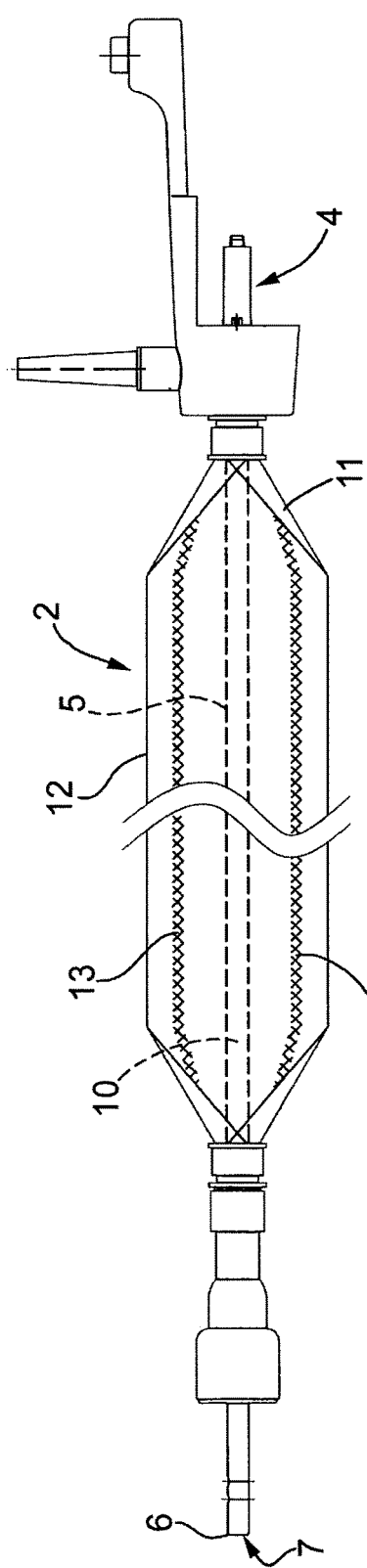
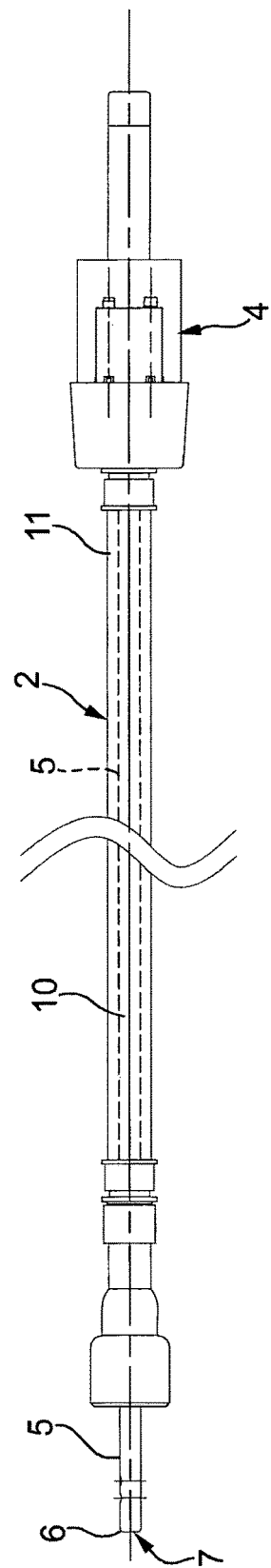
FIG.5
FIG.6

CATHETER FOR TRACHEO-BRONCHIAL SUCTION WITH VISUALIZATION MEANS

TECHNICAL FIELD OF THE INVENTION

The present invention concerns a catheter for tracheo-bronchial suction, especially of the disposable type, with visualization means, i.e. a catheter for tracheal or bronchial suction equipped, in the distal end to be introduced into the patient, with means for displaying the artificial airways and/or the trachea and/or the bronchial tree.

DESCRIPTION OF RELATED ART

Patients kept alive through mechanical ventilators or artificial respirators often require an artificial airway, for example a translaryngeal, tracheostomy or supraglottic tube.

Generally, these patients accumulate fluid secretions in the trachea or in the bronchial tree.

These secretions require periodic removal, which is normally carried out through a procedure that involves: passing a catheter with a small diameter down through the artificial airway in the trachea or in the bronchial tree, applying suction to the catheter through which the secretions are transferred along the inner lumen of the catheter to a collection container.

This procedure is carried out blind without any possibility of displaying and lighting up the position of the distal tip of the catheter.

The state of the art is described in U.S. Pat. No. 4,569,344 and U.S. Pat. No. 4,351,328.

U.S. Pat. No. 4,569,344 describes a device and method for ventilation and suction that integrates in a single unit the selective ability of respiration and of sucking up fluids from the trachea and from the bronchi of a patient.

U.S. Pat. No. 4,351,328 describes another device and method for endotracheal suction of a patient without having to remove the patient from the respirator. A suction tube is positioned in the tracheal tube through a wall of the group of tubes of the respirator, so as to keep the respiration system intact.

However, the devices and methods described in these documents are problematic because they do not allow the patient's secretions to be completely removed.

In particular, it is difficult to selectively position the catheter in the desired region of the tracheobronchial tree and suction directly on the tracheobronchial mucosa can cause damage to the patient.

SUMMARY OF THE INVENTION

The technical task of the present invention is therefore to make a catheter for tracheo-bronchial suction that can be easily introduced in selected areas of the trachea or of the bronchial tree.

In such a technical task, a purpose of the present invention is to make a catheter for tracheo-bronchial suction equipped with a visualization unit that is able to be separated from the catheter.

Such a task and such purposes are all accomplished with a catheter for tracheo-bronchial suction according to one or more of the attached claims.

BRIEF DESCRIPTION OF THE DRAWINGS

These and further advantages will be better understood by any man skilled in the art from the following description and from the attached drawings, given as a non-limiting example, in which:

FIG. 1 shows a rear view of a catheter for tracheo-bronchial suction according to the present invention;

FIG. 2 shows a side view of the catheter for tracheo-bronchial suction according to FIG. 1;

FIG. 3 shows a front view of the catheter for tracheo-bronchial suction according to the previous figures;

FIG. 4 shows a front view of the catheter for tracheo-bronchial suction according to the previous figures without the visualization unit;

FIG. 5 shows a side view of the catheter for tracheo-bronchial suction according to FIG. 4;

FIG. 6 shows a rear view of the catheter for tracheo-bronchial suction according to FIGS. 4 and 5;

DETAILED DESCRIPTION OF PREFERRED EMBODIMENTS

Figure 7:
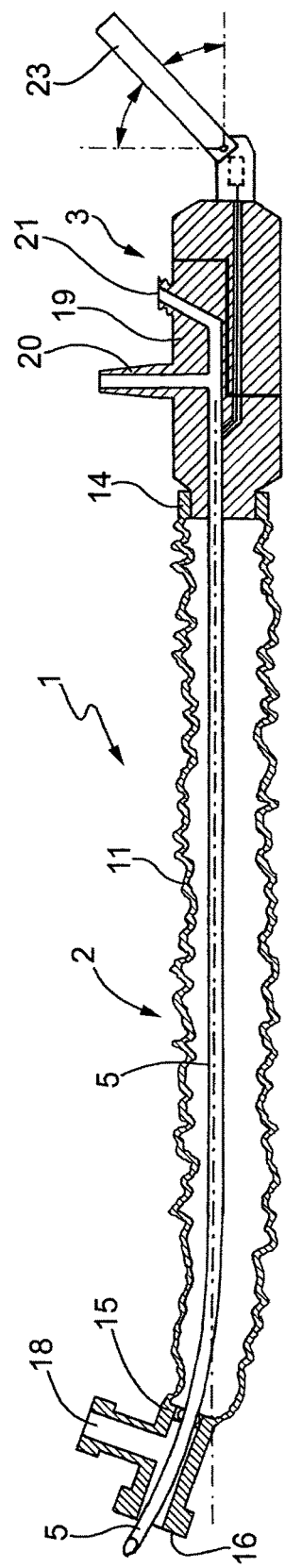
FIG. 7 shows a schematic side section view of the catheter for tracheo-bronchial suction according to the previous figures.
Figure 8:
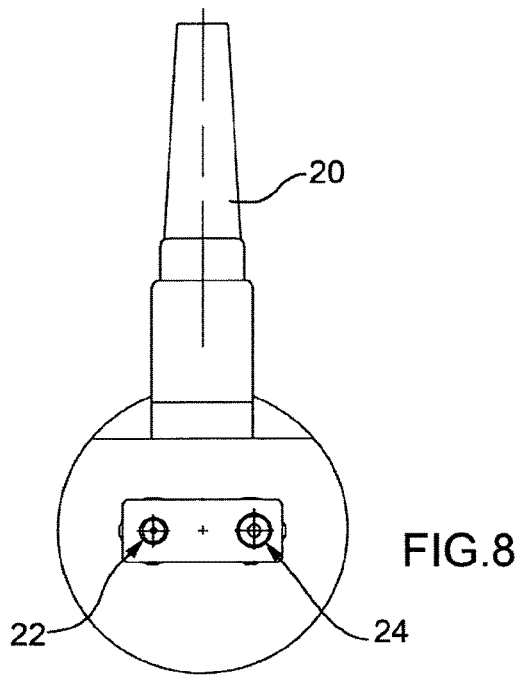
FIGS. 8 and 9 show some details of the connection between the catheter and the visualization unit.
Figure 9:
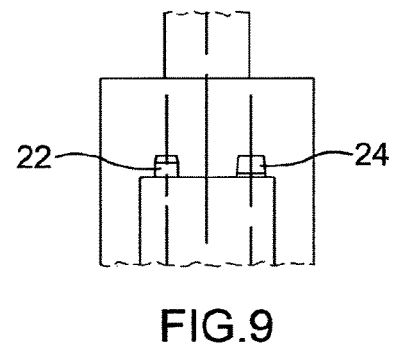

With reference to the drawings, reference numeral 1 wholly indicates the catheter for tracheo-bronchial suction according to the present invention comprising a tubular group 2, in particular of the disposable type, a visualization unit 3 connected to the tubular group 2 through connection means 4.

The tubular group 2 comprises a tubular catheter 5 that comprises a distal end 6 adapted to be introduced into the trachea and/or into the bronchi of a patient to suck up fluid secretions or other similar material needing to be sucked up.

The distal end 6 is therefore rounded and equipped with an opening 7 connected through a tubular channel 10 to suction means suitable for sucking up fluid secretions and/or other similar material that can be found in a patient. In order to increase the possibility of removal of secretions the distal end 6 can also comprise one or more side holes 17 connected to the tubular channel 10.

Figure 10:
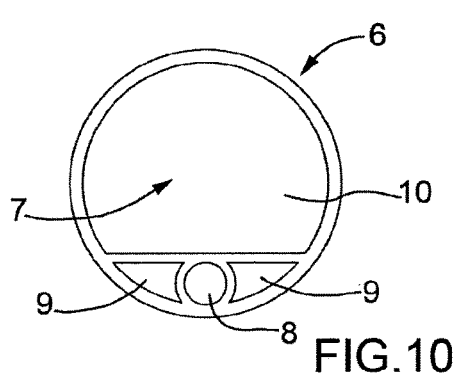
FIGS. 10 and 11 shows two sections of the catheter according to the present invention taken close to the distal tip.
Figure 11:
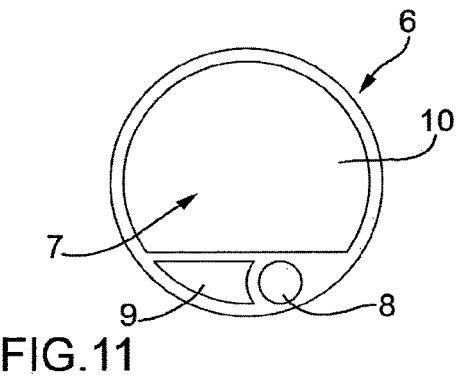

According to what has been illustrated in detail in FIGS. 10 and 11, the distal end 6 comprises viewing means 8 and lighting means 9.

The viewing means 8 can comprise optical fibers suitable for transferring an image, and the lighting means 9 can comprise other optical fibers suitable for guiding light; the aforementioned optical fibers are arranged in tubular channels parallel to the channel 10 through which the fluid secretions pass.

According to another version of the present invention the viewing means 8 can comprise a micro-camera arranged in the distal end 6, and the lighting means 9 can comprise one or more high-efficiency LEDs also arranged in the distal end 6. In this version, there are some cables for supplying power and transmitting images arranged in one or more tubular channels parallel to the channel 10 through which the fluid secretions pass.

Both for the optical fibers and for the micro-camera there is provided a lens made, for example, from plastic.

Moreover, other equivalent technologies can be used for capture and transferring images and for lighting.

As is clear from the figures, it can be seen that the section of the channel 10 through which the fluid secretions pass is much larger than the section of the channels for the transmission of images and for lighting and it is practically slightly smaller than the external section of the catheter.

In particular, the tubular catheter 5 that is introduced into the patient has minimal dimensions, for example it has a diameter of between 4 mm and 8 mm, and therefore it can be withstood by almost all patients. Moreover, in the disposable version it is always ready for use on patients, thus avoiding laborious and expensive sterilization processes.

The tubular group 2 can comprise a fixed or removable sheath or outer coating 11 to keep the tubular catheter 5 not contaminated by external agents during the insertion into or removal from the patient.

In other words, it is possible to carry out many insertions—and removals—of the tubular catheter 5, for example removing the fluid secretions from a patient on many successive occasions, keeping the tubular catheter 5 protected by the coating 11 and thus keeping it not contaminated by external agents even during removal.

According to what is illustrated in FIG. 5, the coating 11 comprises a film 12 that is bent in a tubular shape and welded along a longitudinal welding zone 13.

According to what has been illustrated more specifically in FIG. 7, the coating 11 is connected to the ends 14, 15 so as to completely enclose the tubular catheter 5 in the connection area 3 to the visualization unit and to the duct with the connection 16 to the tracheal tube and the connection 18 to the ventilation circuit.

It should be kept in mind that the casing 11 and the duct with the connection 18 to the ventilation circuit even if illustrated in the figures are completely optional.

Therefore, the catheter 1 for tracheo-bronchial suction according to the present invention, in its most simple version and with regard to the part to be introduced into the patient, can comprise just the tubular catheter 5.

The tubular group 2 comprises a portion 19 equipped with an attachment 20 for suction means, for example a vacuum source, and a hole 21 able to be closed up by the operator to activate the suction. The portion 19 also comprises the connection means 4 that allow a safe connection of the tubular group 2 to the visualization unit 3 to be obtained.

In the disposable version, the entire tubular group 2 comprising the tubular catheter 5, the portion 19 and the connection means 4, is removed and replaced each time the sterility conditions require it, and it should be emphasized that such a replacement also involves the viewing means 8 and the lighting means 9, i.e., according to the versions, the optical fibers suitable for transferring an image and the optical fibers suitable for guiding light or else the microcamera and the high-efficiency LEDs or possible other viewing and lighting devices, including the relative lens.

In any case, such elements are relatively cost-effective and can be replaced each time together with the tubular catheter 5.

The visualization unit 3 is of the type that can be reused many times and comprises a viewer 23 that can be tilted so that the operator can see it better. In the case in which the transmission of images and light takes place through optical fibers, the visualization unit 3 also comprises a microcamera with a CMOS color sensor and at least a high-efficiency white LED arranged close to the connection means 4.

The connection means 4 comprise two attachment elements 22, 24, and such attachment elements 22, 24, being comprised in the connection means 4, are replaced together with the tubular group 2, when in the disposable version this group is replaced.

An important characteristic of the connection means 4 includes the shape of the two attachment elements 22, 24.

An attachment element 22 has a first substantially cylindrical portion and a conical or tapered end portion. The attachment element 22 inserts into a matching seat foreseen in the visualization unit 3, and the shape of this element is such as to allow optimal centering of the image coming from the optical fiber with respect to the microcamera present in the visualization unit 3.

The other attachment element 24 has a frusto-conical attachment that inserts into a corresponding frusto-conical seat foreseen in the visualization unit 3, and in this case the shape is optimal to avoid light dispersions.

According to a version of the present invention, the visualization unit 3 comprises a connection for a module with a power supply unit and a wireless functionality to allow the images to be seen on a separate or remote screen. The visualization unit 3 can also be used with a plurality of other medical devices. The set of the portion 19 and the part of the visualization unit 3 that connects to it constitute a handle 25 by means of which the operator can comfortably grip and orient the catheter.

An important characteristic of the present invention is indeed given by the possibility of orienting and directing the tubular catheter 5 selectively in the trachea and/or the bronchi.

According to a version of the present invention, the tubular catheter 5 has a curvature along the longitudinal axis of the catheter, for example in an intermediate position or close to the distal end 6, to allow the end of the catheter to be directed by rotating the catheter around its longitudinal axis.

According to another version of the present invention, the tubular catheter 5 has a mechanism for guiding the distal end 6 of the catheter.

According to yet another version of the present invention, the tubular catheter 5 has a guiding mechanism through which the catheter is made with a certain curvature and there are means for straightening the catheter that use a chuck, a wire, a tube or a rectilinear shaped reinforcer that can be reversibly inserted along the tubular catheter 5 or in a separate channel inside the tubular catheter itself.

According to a further version of the present invention, the tubular catheter 5 is entirely or partially made with a material that has a permanent or temporary memory, so that the tube can be modelled, before insertion into the patient.

In order to effectively transmit the rotation to the distal end 6, the tube of the tubular catheter 5 has special constructive characteristics.

The distal end 6 is relatively flexible and has a tubular section with relatively thin walls. The central and proximal part of the tube of the tubular catheter 5 is more rigid against twisting so as to transmit the rotations applied to the user through the handle 25.

In order to obtain the greater rigidity of the central and proximal part, the tube of the tubular catheter 5 can be made with a greater thickness in such central and proximal parts, for example by wrapping it on the outside with another: tube for a certain longitudinal portion, or else by adding material during the manufacturing process, for example during extrusion, so as to obtain a slightly frusto-conical shape, or else by loading the material of the tube with materials capable of stiffening the structure especially with respect to twisting. Moreover, the tube can be made with greater thickness and therefore mechanically machined to obtain a slightly frusto-conical shape.

Figure 12:
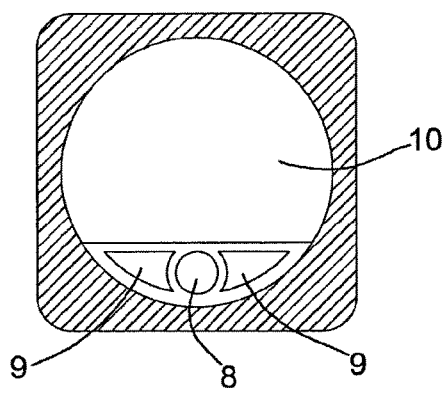
FIGS. 12 and 13 show two sections of the catheter according to the present invention taken in the central portion of the catheter.
Figure 13:
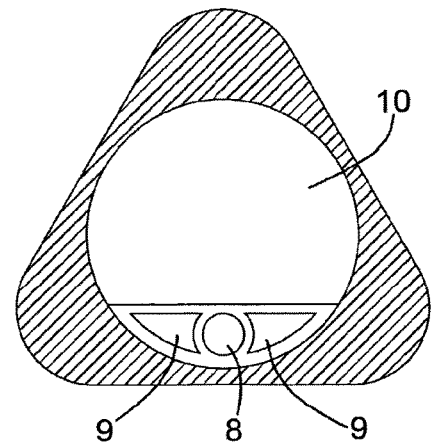
Figure 14:
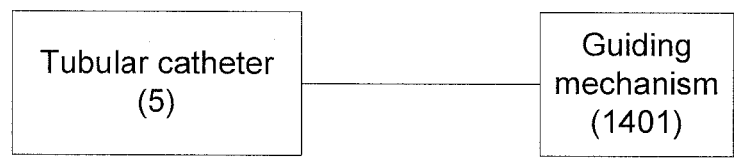
FIG. 14 is an exemplary schematic diagram of a tubular catheter according to the present invention.

According to what has been illustrated in FIGS. 12 and 13 the shape in section can also be varied, for example with a square or triangular shape with rounded corners.

In this case, the tube is made firstly in a cylinder shape and then is heat; moulded in moulds with a square or triangular section with rounded corners.

The tube of the tubular catheter 5 can be made from plastic material suitable for medical use, for example medical PVC (polyvinylchloride).

Thanks to the present invention, the operator can view a visualization to identify the position of the end of the catheter and the artificial airways, the trachea and the bronchial tree.

This offers advantages with respect to the state of the art. With the visualization, it is possible to ensure that the catheter is adjacent to or inside collections of liquid secretions or other material and then apply the suction.

The suction can be applied selectively in order to avoid lesions to the mucosa and to facilitate the more complete elimination of the secretions.

The catheter according to the present invention also allows viewing to diagnose intra-bronchial and tracheal pathologies and allows the accumulation of secretions in the artificial respiratory ways to be identified. The present invention has been described according to preferred embodiments, but equivalent variants can be devised without departing from the scope of protection offered by the claims.

The invention claimed is:

1. A catheter for trachea-bronchial suction comprising:
    a disposable catheter comprising a tubular body having a proximal and a distal end;
    a suction channel extending through the tubular body of the catheter and equipped to be connected to a vacuum source;
    a handle coupled to the proximal end of the tubular body and having two attachment elements each having a different shape from the other, wherein one attachment element has a first substantially cylindrical portion and a tapered end portion and the other attachment element has a frusto conical attachment;
    a visualization unit removably connected to said tubular catheter by the two attachment elements, the visualization unit comprising a light source, a camera and a viewer, wherein the tubular body of the catheter is made with a greater thickness in central and proximal parts of the tubular body relative to a distal part of the tubular body, wherein a cross-section of the central part of the tubular body is one of a substantially square or triangular shape and a cross-section of the distal end of the tubular body is of a substantially circular shape, so as to stiffen the tubular body and enable the tubular body to resist twisting, and wherein the tubular body includes optical fibers extending to the distal end for transferring images and light between the visualization unit and the distal end.

2. The catheter according to claim 1, wherein said tubular body further comprises a lighting means positioned in the distal end.

3. The catheter according to claim 2, wherein the lighting means positioned in the distal end comprises optical fibers suitable for transmitting light, or else one or more high-efficiency LEDs.

4. The catheter according to claim 1, wherein the visualization unit is of a type that can be reused many times.

5. The catheter according to claim 1, wherein the visualization unit comprises a connection for a module with a power supply and a wireless functionality to allow images to be seen on a separate or remote screen.

6. The catheter according to claim 1, comprising a fixed or removable sheath or outer coating to keep the tubular body sterile during conservation or storage, and in use to protect the tubular body during insertion into a patient.

7. The catheter according to claim 6, wherein said sheath or outer coating comprises a duct with a connection to a tracheal tube and a connection to a ventilation circuit.

8. The catheter according to claim 1, wherein said tubular body is made entirely or partly with a material that has a permanent or temporary memory, so that a tube can be modeled, before insertion into a patient.

9. The catheter according to claim 1, wherein said tubular body is made with a greater thickness in the central and proximal parts of the tubular body by wrapping it externally with another tube for a certain longitudinal portion, or by adding material during a manufacturing process, or by loading the material of the tubular body with materials able to stiffen the tubular body with respect to twisting.

10. The catheter according to claim 1, wherein said tubular body is made with greater thickness and thus mechanically machined to obtain a slightly frusto-conical shape.

11. The catheter according to claim 1, wherein said tubular body comprises a square or triangular shape in section with rounded corners.

12. The catheter according to claim 1, wherein the handle is suitable for giving rotations and movements to the tubular body.

13. The catheter according to claim 1, wherein the two attachment elements include a first attachment element comprising a first substantially cylindrical portion and a conical or tapered end portion, said first attachment element being able to be inserted into a matching seat provided in the visualization unit.

14. The catheter according to claim 1, wherein the two attachment elements include a second attachment element comprising a frusto-conical attachment able to be inserted into a corresponding frusto-conical seat provided in the visualization unit.

15. The catheter according to claim 1, wherein said tubular body comprises, in its distal end, one or more side holes connected to the suction channel.

16. The catheter according to claim 1, wherein the visualization unit can be used with a plurality of other medical devices.

17. A catheter for trachea-bronchial suction comprising:
    a catheter of a disposable type, comprising a tubular body having a proximal and a distal end;
    a suction channel extending through the tubular body of the catheter and equipped to be connected to a vacuum source;
    a visualization unit removably connected to said tubular body through attachment elements, wherein said tubular body comprises a curvature along a longitudinal axis of the tubular body, in an intermediate position or close to the distal end, to allow the distal end of the tubular body to be directed by rotating the tubular body around its longitudinal axis, wherein said tubular body is made with a greater thickness in a central and proximal parts of the tubular body relative to the distal end of the tubular body, wherein a cross-section of the central part of the tubular body is one of a substantially square or triangular shape and a cross-section of the distal end of the tubular body is of a substantially circular shape so as to stiffen the tubular body and enable the tubular body to resist twisting.

18. A catheter for trachea-bronchial suction comprising:

a disposable catheter, comprising a tubular body having a proximal and a distal end;

a suction channel extending through the tubular body of the catheter and equipped to be connected to a vacuum source;

a visualization unit removably connected to said disposable catheter through attachment elements, the visualization unit comprising a light source, a viewer, wherein a said tubular body is made with a greater thickness in a central and proximal parts of the tubular body relative to the distal end of the tubular body, wherein a cross-section of the central part of the tubular body is one of a substantially square or triangular shape and a cross-section of the distal end of the tubular body is of a substantially circular shape, so as to stiffen the tubular body and enable the tubular body to resist twisting, and wherein the tubular body includes a camera positioned on the distal end, optical fibers extending to the distal end for transferring light between the visualization unit and the distal end and electronic wires for transmitting a visualization signal between the visualization unit and the camera on the distal end.

* * * * *